United States Patent [19]

Pisarik

[11] Patent Number: 5,415,647
[45] Date of Patent: May 16, 1995

[54] FLEXIBLE, MULTI-GROOVED VASCULAR IMMOBILIZER

[76] Inventor: Paul Pisarik, 4154 W. Corona Dr., Chandler, Ariz. 85226-7222

[21] Appl. No.: 306,886
[22] Filed: Sep. 15, 1994
[51] Int. Cl.⁶ ............................................. A61M 5/00
[52] U.S. Cl. ........................................ 604/115; 604/180
[58] Field of Search ............... 604/115, 116, 174, 179, 604/180; 128/DIG. 26

[56] References Cited

U.S. PATENT DOCUMENTS

| | | |
|---|---|---|
| 1,561,116 | 11/1925 | Silliman . |
| 1,824,516 | 9/1931 | Tyvand ................................ 128/327 |
| 2,008,340 | 7/1935 | Salvati et al. ...................... 128/215 |
| 2,103,174 | 12/1937 | Posada ............................... 128/215 |
| 2,234,961 | 3/1941 | Canada ............................... 128/327 |
| 3,324,854 | 6/1967 | Weese ................................ 128/215 |
| 4,196,735 | 4/1980 | Ayer .................................. 128/327 |
| 4,314,568 | 2/1982 | Loving ............................... 128/327 |
| 4,316,461 | 2/1982 | Marais et al. ...................... 128/214 R |
| 4,332,248 | 6/1982 | DeVitis ............................. 128/214 R |
| 4,408,611 | 10/1983 | Enjoji ................................ 604/116 |
| 4,586,924 | 5/1986 | Lanning ............................ 604/115 |
| 4,988,062 | 1/1991 | London ............................ 128/DIG. 26 |
| 5,112,312 | 5/1992 | Luther ............................. 128/DIG. 26 |
| 5,147,307 | 9/1992 | Gluck ............................... 604/116 |
| 5,192,271 | 3/1993 | Kalb et al. ........................ 604/116 |
| 5,226,892 | 7/1993 | Boswell ............................ 604/180 |
| 5,254,095 | 10/1993 | Harvey ............................ 604/115 |

Primary Examiner—Paul J. Hirsch

[57] ABSTRACT

An immobilizer for blood vessels including multiple grooves on the bottom surface of a clear, flexible length of a plastic material, arranged in parallel to each other and perpendicular to the length of the plastic material. The grooves are of varying sizes to accommodate the differing diameters of veins and the walls of the grooves are of varying angles to accommodate veins of differing depths.

14 Claims, 6 Drawing Sheets

FLEXIBLE, MULTI-GROOVED VASCULAR IMMOBILIZER

BACKGROUND

1. Field of Invention

This machine relates to a medical apparatus, specifically to an improved medical apparatus to immobilize a vascular structure so that it may be punctured with a needle.

2. Description of Prior Art

The piercing of body conduits, namely arteries and veins, is necessary at times for obtaining specimens for analysis, administration of fluids and medications, transfusion of blood, etc. It takes a considerable amount of skill to be able to locate the conduit, immobilize it, and then insert the needle so as to minimize pain to the patient.

There are multiple problems inherent in this procedure. These conduits, especially veins, are difficult to hold steady. They tend to "roll" (move laterally) when the needle is being inserted. If the needle does get inserted into the vein, the vein may collapse. If the needle is inserted and then advanced, the needle may go through the vein wall because of the serpentine nature of this type of blood vessel. Then the blood in the vein, or the intravenous fluid being introduced, extravasates into the surrounding tissues, causing swelling, bruising, and pain.

When these events occur, it is necessary to start again. Because of these multiple punctures,
1) the patient experiences more discomfort and anxiety,
2) there is an increased chance for infection,
3) there are a decreased number of sites for immediate intravenous access,
4) the operator requires additional time, and
5) there are added expenses because of the extra supplies needed.

The operator may try to immobilize the vein with his or her fingers. This however is fraught with the danger of the operator puncturing one of his or her fingers with the needle and being subject to all the attendant risks of getting blood borne diseases such as hepatitis B and HIV infections as well as bacterial infections at the puncture site.

Multiple devices have been invented to immobilize vascular structures in the past. None are now in widespread clinical use, as all have major problems that limit their usefulness as detailed below.

One of the first vascular stabilizing devices is shown in U.S. Pat. No. 1,561,116 (Silliman) which discloses a hand held vein stabilizer having a fiat plate with a notch. The plate is placed on the skin, with the notch placed over a vein and directed proximally toward the heart.

The difficulties with this device are that
1) it is flat and rigid and does not conform to the surface of the body where the vein to be punctured lies,
2) it has one sized notch so it cannot be adjusted for the caliber of the vein,
3) it is unwieldy to use, and
4) it is only good for very superficial veins with minimal subcutaneous tissue. Here it is easy to get around the vein and immobilize it bilaterally (although it may still move when a needle tries to puncture it). But deeper blood vessels have more intervening skin and subcutaneous structures so the pressure is more superior than bilateral and the vein can still move laterally and "roll". Also this pressure can flatten the vein, making it harder to puncture. This is a major limitation of a rigid notched device and I'll refer to it as such in several of the following patents.

U.S. Pat. No. 1,824,516 (Tyvand) discloses a vein retainer including a complex flat metal structure that is placed over a vein and held there by tourniquets. It has two opposing sliding metal plates with facing downcurving edges that can be made to move toward each other, with the downcurving edges immobilizing the vein.

The difficulties with this device are that
1) it is flat and rigid and does not conform to the surface of the body where the vein lies,
2) it would be too expensive to manufacture to be disposable, so it would have to be sterilized before each use,
3) it uses tourniquets to position the vein retainer over the vein; this greatly limits the location of the veins that may be used since the vein has to be in such a location where the whole device can be placed on the extremity,
4) it is complicated to manufacture, and
5) it is relatively complicated to use.

U.S. Pat. No. 2,103,174 (Posada) discloses a 'V' shaped metal device that is located at one end of a tourniquet. This metal device has a notch in the center of the 'V' to immobilize the vein to be punctured. By pushing in the center of the device to flatten the 'V', the notch in the center can get smaller and accommodate different sized veins.

The difficulties with this device are that
1) it takes coordination to operate the spring mechanism of the metal plate and keep it under constant tension so that the sides of the notch are up against the sides of the vein, without collapsing the vein,
2) it can induce operator fatigue, and
3) it will not immobilize smaller caliber veins very well.

U.S. Pat. No. 2,234,961 (Canada) discloses a complex mechanism consisting of a tourniquet on top of which is attached a pivoted metal device. This device has two downsloping legs that can be positioned to press on either side of the vein to be punctured.

The difficulties with this device are that
1) it would be too expensive to manufacture to be disposable, so it would need to be sterilized before each use,
2) the vein immobilizer is connected to a tourniquet thereby limiting the areas on the body where a vein could be used to those where the tourniquet could be applied in close proximity to the vein,
3) there is a fixed distance between the two downsloping legs so it cannot be adjusted for the caliber of the vein,
4) it has the limitations of a rigid notched device as detailed under the above Silliman reference,
5) it is complicated to manufacture, and
6) it is complicated to use.

U.S. Pat. No. 3,324,854 (Weese) discloses a device to be attached to the barrel of a syringe to immobilize a vein. This device has a notch in it to immobilize the vein to be punctured.

The difficulties with this device are that
1) it has one sized notch so it cannot be adjusted for the caliber of the vein, 2) it has to be used with a syringe, which limits its usefulness (i.e., it cannot be used with those needles used to start intravenous lines),
3) it would be too expensive to manufacture to be disposable so it would need to be sterilized before each use, and
4) it has the limitations of being a rigid notched device as initially detailed under the above Silliman reference.

U.S. Pat. No. 4,196,735 (Ayer) discloses a fiat device with two descending legs to hold down an artery by pressing down on both sides of the artery.

The difficulties of this device are that
1) there is a fixed distance between the two descending legs of the device so it cannot be adjusted for the caliber of the blood vessel,
2) it has the limitations of being a rigid notched device as mentioned in the above Silliman reference, and
3) it is rigid and does not conform to the area of the body where the blood vessel is.

U.S. Pat. No. 4,314,568 (Loving) discloses a fiat plate with a slot in the center, the two halves of which can move together to accommodate different sized veins. The device is attached to a tourniquet to dilate the vein to be punctured.

The difficulties with this device are that
1) it does not conform very well to different surfaces of the body where the vein may lie,
2) it is associated with a tourniquet, which limits the area of the body where a vein could be used to those areas where the tourniquet could be applied in close proximity to the vein,
3) it is hard to use with small caliber veins, and
4) it would not be useful to immobilize deeper veins.

U.S. Pat. No. 4,316,461 (Marais et al.) discloses a fiat, rigid base plate with a major longitudinal notch and groove to embrace a vein. Once the intravenous needle is introduced, the whole assembly is held in place with a pair of straps after the intravenous tubing is attached to the plate.

The difficulties with this device are that
1) it is rigid and fiat—not conforming to the body surface where the vein is located,
2) the groove and slot are too long to straighten and immobilize serpentine veins,
3) its design limits it to those areas of the body where the straps can be placed on an extremity,
4) it has only one sized groove so it cannot be adjusted for the caliber of the vein,
5) it has the limitations of being a notched device as initially mentioned under the above Silliman reference,
6) it is complicated to manufacture, and
7) it is difficult to use.

U.S. Pat. No. 4,332,248 (DeVitis) discloses a device comprised of a long parallel pair of members. These members prevent the lateral movement of a vein while the vein is being pierced with a needle.

The difficulties with this device are that
1) it is too long to straighten and immobilize serpentine veins,
2) as it is designed, the needle actually punctures the unstabilized part of the vein, away from the parallel members,
3) it is made of only one sized parallel members so it cannot be adjusted for the caliber of the vein,
4) it does not conform to the body surfaces where the vein lies, and
5) it has the limitation of being a rigid notched device as initially discussed under the above Silliman reference.

U.S. Pat. No. 4,586,924 (Lanning) discloses a fiat plate with a notch at one end. This notch leads to a groove under the plate. This combination immobilizes a vein.

The difficulties with this device are that
1) it is flat and rigid limiting its use on different surfaces of the body,
2) it has one sized groove so it cannot be adjusted to the caliber of the vein,
3) the groove and notch are too long to straighten and immobilize serpentine veins, and
4) it has the limitations of being a notched device as initially mentioned under the above Silliman reference.

U.S. Pat. No. 5,254,095 (Harvey) discloses a stabilizer for blood vessels that looks like a shortened, widened forceps and functions similarly.

The difficulties with this device are that
1) it will not immobilize smaller caliber veins very well,
2) it requires coordination to apply constant tension to the divergent panels without collapsing the vein, and
3) it can induce operator fatigue.

Thus there is a great need for a vascular stabilizer that overcomes all the disadvantages listed in the above prior patents and this will be described below.

SUMMARY OF THE INVENTION

Accordingly, several objects and advantages of my invention are to provide a vascular immobilizer that
(a) is flexible so it can contour to different body surfaces—hands, feet, arms, legs, scalp, neck, etc.;
(b) is made of a clear flexible material so veins can be seen in the device;
(c) is made of one simple piece;
(d) is easy to manufacture;
(e) is easy to use;
(f) is easy to hold the vein to be punctured in place after it is stabilized by the immobilizer—a person can use one to two fingers of one hand to exert mild pressure on the immobilizer;
(g) has various sized grooves to accommodate a wide variety of different sized blood vessels;
(h) can immobilize veins at different depths under the surface of the skin;
(i) immobilizes a vein on three sides—bilaterally and superiorly;
(j) is disposable so it will not need resterilization;
(k) is independent of the positioning of a tourniquet so it has greater flexibility in choosing a vein to immobilize;
(l) has grooves short enough to be able to straighten out superficial serpentine veins;
(m) can be used to immobilize small caliber veins;
(n) immobilizes a vein so that it may be punctured with a syringe or other needle devices;
(o) is inexpensive to manufacture;
(p) increases the speed of obtaining a venipuncture;
(q) decreases the discomfort of obtaining a venipuncture since fewer tries would be needed; and
(r) decreases the cost since there would be fewer sticks and fewer supplies needed.

Briefly described, the present invention is an improved vascular immobilizer consisting of a flexible, flat, elongated piece of a clear plastic or plastic-like material with multiple grooves of varying caliber on the undersurface, arranged parallel to each other and perpendicular to the longitudinal axis of the immobilizer. The immobilizer can not only engage veins of differing calibers but also of differing depths because the walls of these grooves have three different angles to accommodate veins of differing depth.

Still, further objects and advantages will become apparent from a consideration of the ensuing description and accompanying drawings.

DETAILED DESCRIPTION OF THE PREFERRED EMBODIMENT

Referring more specifically to the drawings, and with particular reference to FIGS. 1-4, the vascular immobilizer 66 is preferably made from an elongated piece of clear flexible plastic material. The plastic material needs to be clear so that the vein can be "captured" and easily seen in vascular immobilizer 66. This allows easier insertion of the needle. Vascular immobilizer 66 is flexible so that the grooves can be widened and placed on top of the vein to hold it in place. The plastic material is preferentially sufficiently elastic that when bent, returns to its original shape. The bottom surface of vascular immobilizer 66 has various sized grooves arranged parallel to each other and perpendicular to the longitudinal axis of immobilizer 66 to immobilize veins of varying diameter. The grooves also have walls of varying slope to be able to accommodate veins of varying depth beneath the surface of the skin. The height and depth of vascular immobilizer 66 are "tapered", i.e., they both decrease from the side with the larger grooves to the side with the smaller grooves. The edges of vascular immobilizer 66 are beveled, with the top surface 62 being smaller than the bottom surface 64.

Figure 1:
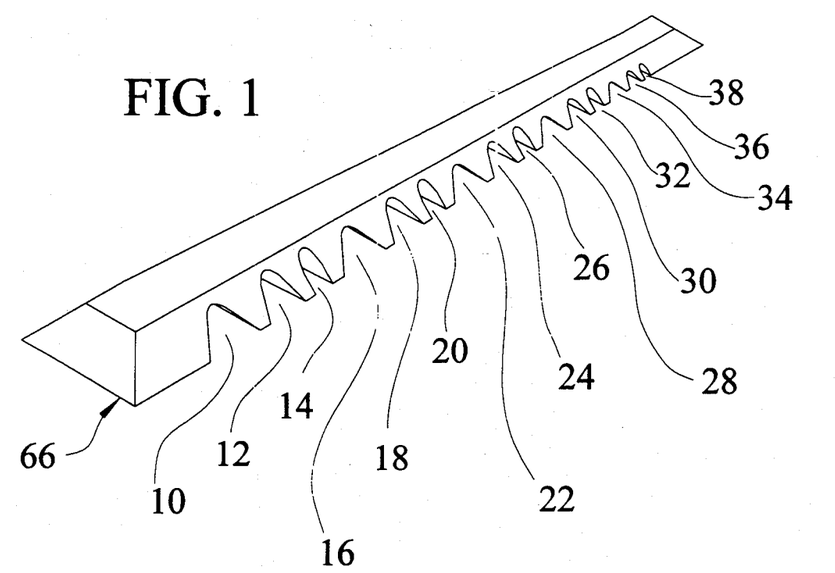
FIG. 1 is a perspective view of the immobilizer taken from the forward end thereof.
Figure 2:
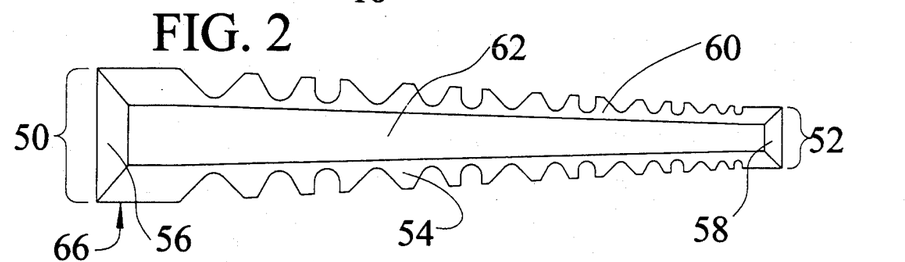
FIG. 2 is a top elevational view thereof.
Figure 3:
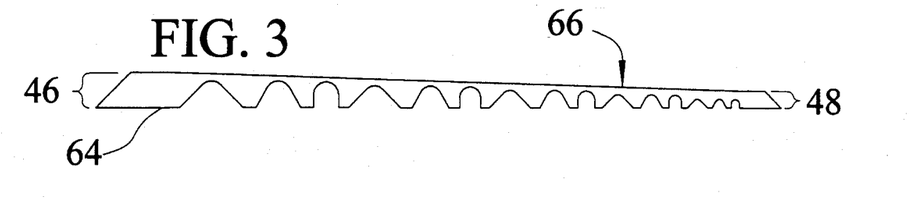
FIG. 3 is a front end elevational view thereof.
Figure 4:
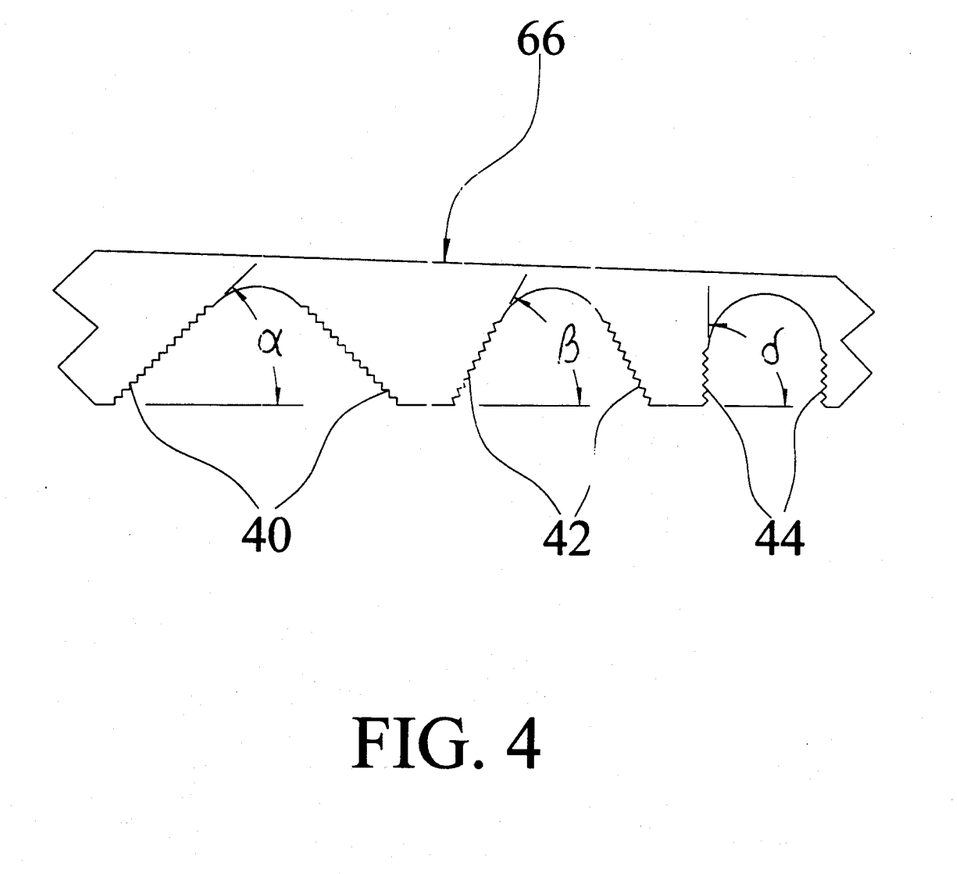
FIG. 4 is a front end elevational view of a portion of the vascular immobilizer.

FIG. 1 shows a perspective view of vascular immobilizer 66 taken from the forward end thereof, FIG. 2 shows the top end elevational view, FIG. 3 shows the front end elevational view, and FIG. 4 shows the front end elevational view of a portion of vascular immobilizer 66.

Bottom surface 64 has formed therein various shaped and sized grooves 10, 12, 14, 16, 18, 20, 22, 24, 26, 28, 30, 32, 34, 36, 38.

Grooves 14, 20, 26, 32, 38 are designed to immobilize "superficial" veins of varying diameter. The radius of the arc of the top portion of these grooves varies from 1 mm to 3 mm. These grooves have walls 44 that are perpendicular to the bottom surface of immobilizer 66 (angle delta=90 degrees in FIG. 4). These walls can laterally support a superficial vein. Walls 44 also have a roughed texture so as to be better able to grip the skin surface surrounding the vein. The top portion of such a groove immobilizes the vein superiorly. The height of such grooves varies from 2 mm to 6 mm.

Grooves 10, 16, 22, 28, 34 are designed to immobilize "deep" veins of varying diameter. The radius of the arc of the top portion of these grooves varies from 1 mm to 3 mm. These grooves have walls 40 that are at an approximate 45 degree angle to the bottom surface of the immobilizer (angle alpha equals 45 degrees in FIG. 4). This increases the spread of the groove so that it can get a better bite to immobilize a deeper vein. Walls 40 also have a roughed texture so as to be able to better grip the skin surface above the deep vein. The top portion of the groove immobilizes the vein superiorly. The height of the grooves varies from 2 mm to 6 mm.

Grooves 12, 18, 24, 30, 36 are designed to immobilize "intermediate depth" veins of varying diameter. The radius of the arc of the top portion of these grooves varies from 1 mm to 3 mm. These grooves have walls 42 that are at an intermediate angle compared to the above two types of grooves—approximately 60 degrees to the bottom surface of the immobilizer (angle beta equals 60 degrees in FIG. 4). Walls 42 of these grooves also have a roughed texture so as to be able to better grip the skin surface above the intermediate depth vein. The top portion of the groove immobilizes the vein superiorly. The height of the grooves varies from 2 mm to 6 mm.

As illustrated, the height and width of vascular immobilizer 66 decrease from the end that has the larger grooves to the end that has the smaller grooves (height 46 is greater than height 48 and width 50 is greater that width 52). This decrease in height is necessary so that the distance between the top of the groove and top surface 62 stays the same or decreases slightly. This is necessary so that the groove can open up easily when vascular immobilizer 66 is bent away from the skin surface just above the groove. The decrease in width makes it easier for vascular immobilizer 66 to "straighten out" smaller caliber veins since the length of the smaller caliber vein inside immobilizer 66 is more proportional to its decreased cross-sectional area.

The front surface 54, side surfaces 56 and 58, and back surface 60 are beveled at approximate a 45 degree angle so that top surface 62 is smaller than bottom surface 64. This allows the operator to be able to insert the needle 80 (FIG. 6) into a point on the vein that is at least partially immobilized at the point of puncture.

Figure 5A:
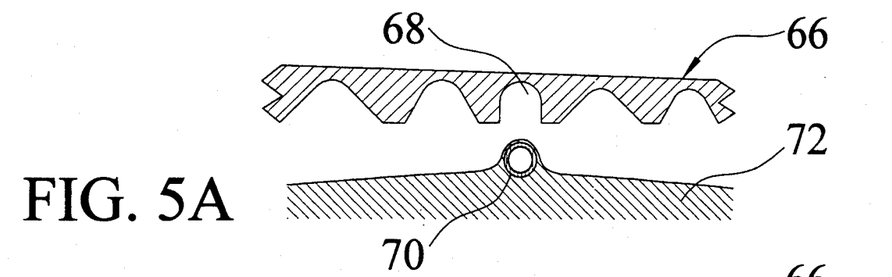
FIGS. 5A to 5D are partial sectional views that show the process of immobilizing a superficial vein through cross-sectional views of the vascular immobilizer (taken vertically down the longitudinal axis of the immobilizer) and the superficial vein and subcutaneous structures.
Figure 5B:
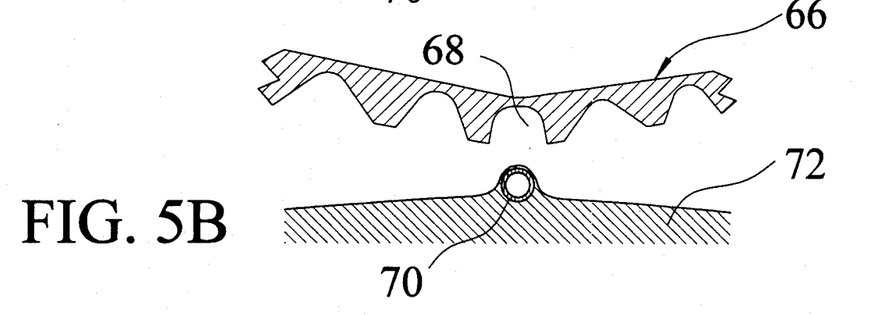
Figure 5C:
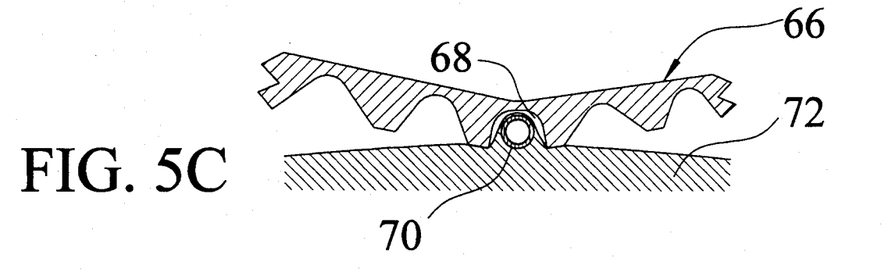
Figure 5D:
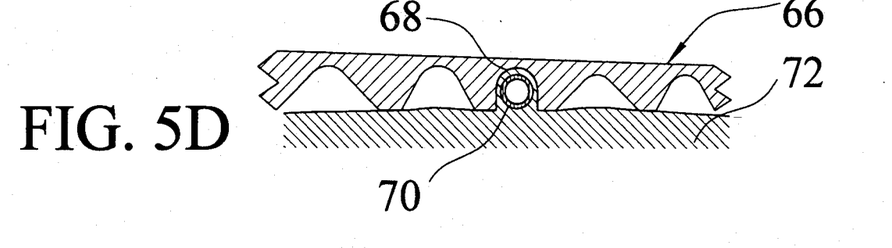
Figure 6:
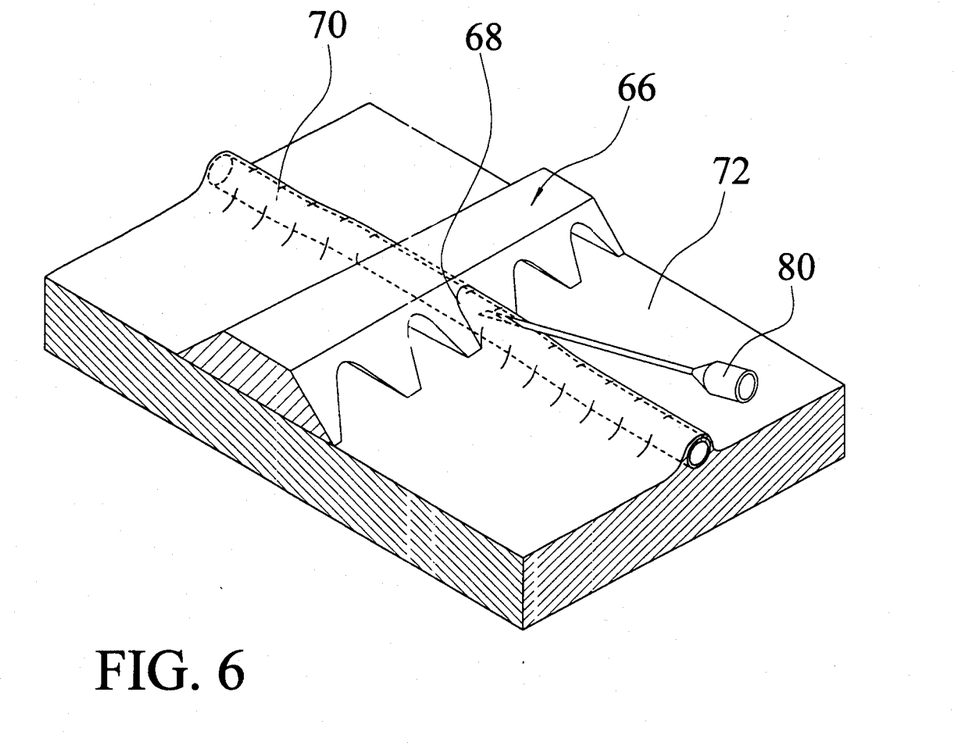
FIG. 6 is a perspective view of a portion of the immobilizer immobilizing a superficial vein taken from the forward end thereof and shows the final process of inserting a needle into the superficial vein.

FIGS. 5A to 5D show how to use vascular immobilizer 66 to immobilize a superficial vein 70. The operator finds a superficial groove 68 that is of the appropriate size as shown in FIG. 5A. He or she then bends that section of vascular immobilizer 66 above groove 68 away from the surface of the skin and subcutaneous structures 72 so that superficial groove 68 opens up to a widened configuration as shown in FIG. 5B. Widened superficial groove 68 is then placed over superficial vein 70 as shown in FIG. 5C. Vascular immobilizer 66 is then relaxed and allowed to rest on top of skin surface 72. This holds superficial vein 70 snugly inside the now relaxed superficial groove 68, as shown in FIG. 5D and FIG. 6. Then mild pressure with one hand can be used to hold immobilizer 66 in this configuration while needle 80 then is introduced into superficial vein 70 with the other hand, at a point close to immobilizer 66 as shown in FIG. 6.

Figures 7A, 7B, 7C:
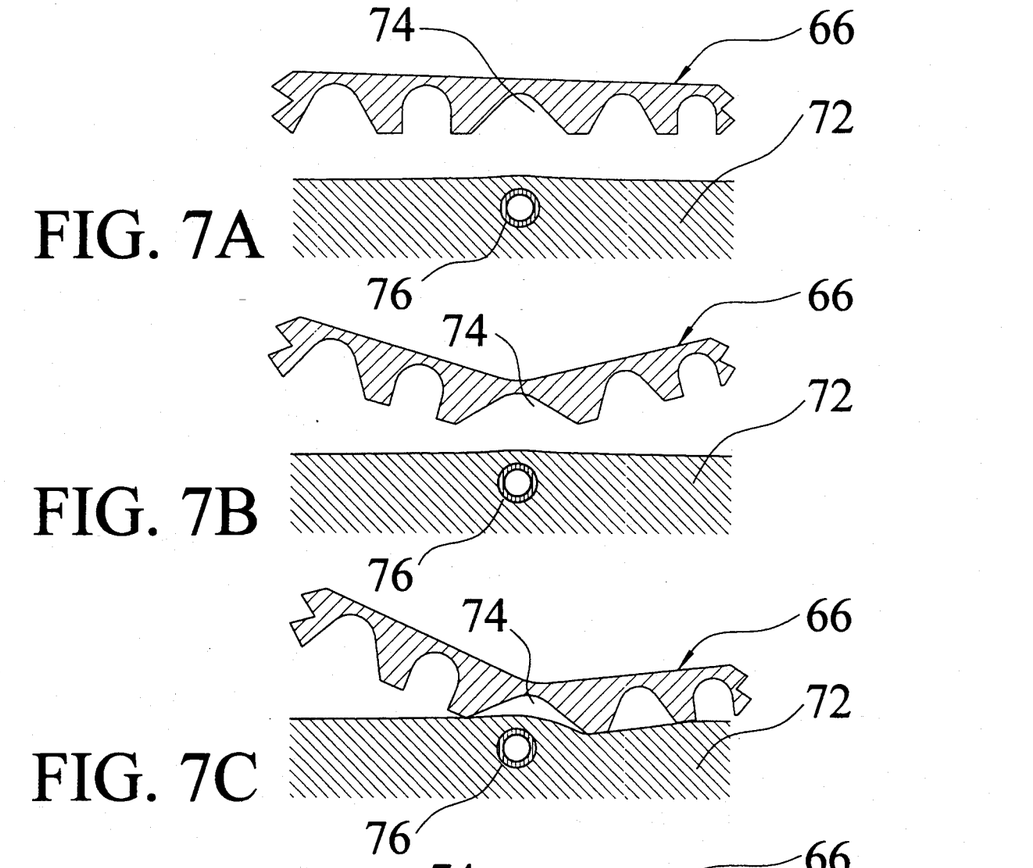
FIGS. 7A to 7E are partial sectional views that show the process of immobilizing a deep vein through cross-sectional views of the vascular immobilizer (taken vertically down the longitudinal axis of the immobilizer) and the deep vein and subcutaneous structures.
Figures 7D, 7E:
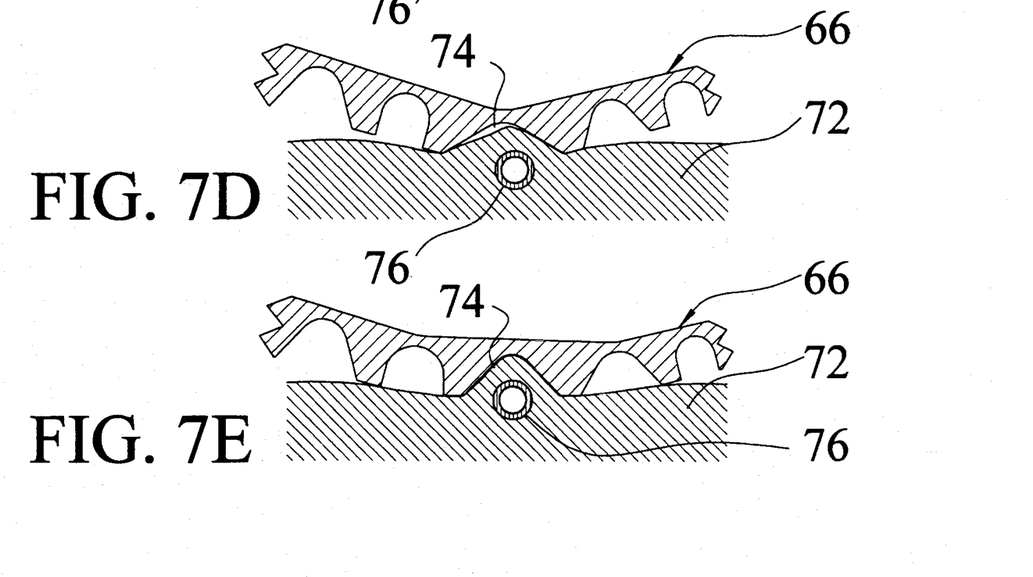
Figure 8:
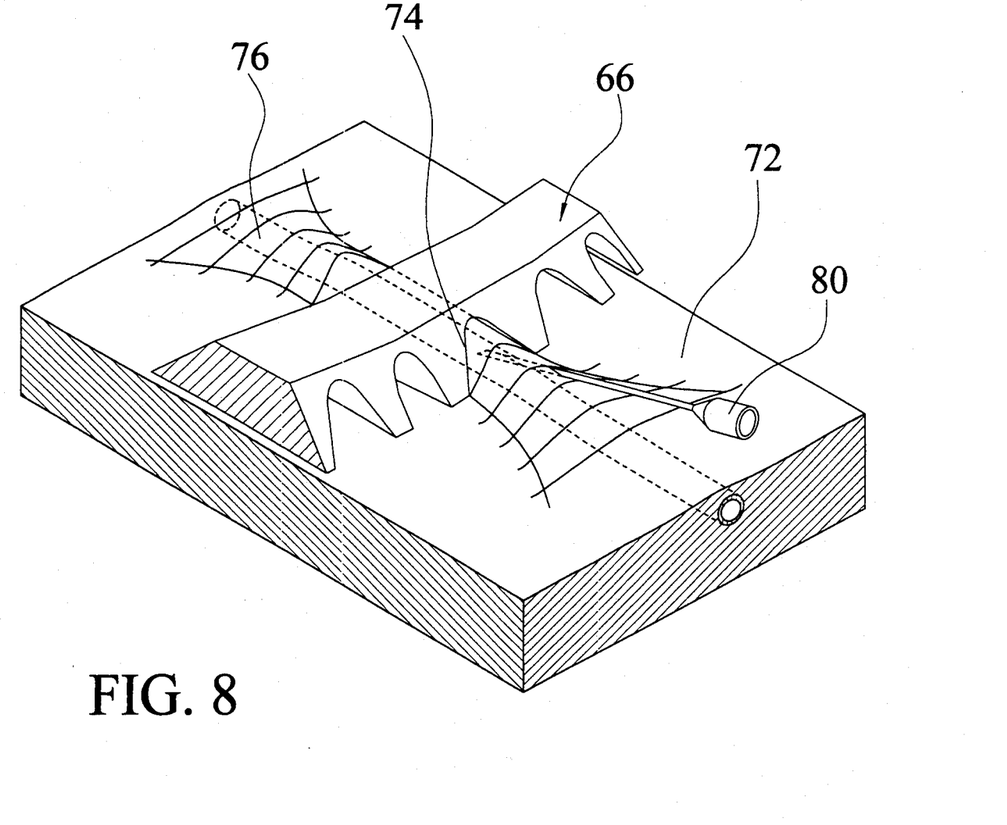
FIG. 8 is a perspective view of a portion of the immobilizer immobilizing a deep vein taken from the forward end thereof and shows the final process of inserting a needle into the deep vein.

FIGS. 7A to 7E show how to use vascular immobilizer 66 to immobilize a deep vein 76. (The procedure for a vein of intermediate depth would be the same except an intermediate depth groove would be used). The operator finds a deep groove 74 that is of the appropriate size as is shown in FIG. 7A. The operator then bends that section of vascular immobilizer 66 away from skin surface 72, so that deep groove 74 opens up into a widened configuration, as shown in FIG. 7B. One edge of widened deep groove 74 is placed on skin surface 72 at one side of deep vein 76, as shown in FIG. 7C. Then skin surface 72 is "puckered" by pushing vascular immobilizer 66 toward the opposite side of deep vein 76 so that as much of skin surface 72 as possible can be placed inside widened deep groove 74. The opposite edge of widened deep groove 74 is then pressed firmly on skin surface 72 on the opposite side of deep vein 76, as shown in FIG. 7D. Then vascular immobilizer 66 is relaxed and straightened out so widened deep groove 74 closes up back to its original shape 74. It is then brought to a position over deep vein 76, as shown in FIG. 7E and FIG. 8. Then mild to moderate pressure is exerted on immobilizer 66 with one hand, so that deep vein 76 is held in place, while needle 80 is introduced into deep vein 76 with the other hand as is shown in FIG. 8.

Accordingly, it can be seen that the vascular immobilizer of the present invention can immobilize veins of different calibers and depths beneath the skin more effectively than the immobilizers of the prior art. This decreases the time to obtaining a successful venipuncture and decreases the discomfort, anxiety, and cost to the patient because of the fewer number of attempts to successful venipuncture.

Furthermore, the vascular immobilizer has additional advantages in that it is easy and inexpensive to manufacture being of one piece of clear, flexible plastic;

it is easy to use, requiring minimal manipulation and coordination;

it can be used on any body surface;

it can be used without a fixed spatial relationship to a tourniquet;

it immobilizes the vein on three sides—bilaterally and superiorly;

it can straighten out superficial veins thus aiding in insertion of intravenous lines;

it is disposable; and it does not require attachment to the barrel of a syringe.

Although the description above contains many specificities, these should not be construed as limiting the scope of the invention but as merely providing illustrations of the presently preferred embodiment of this invention. Various other embodiments and ramifications are possible within it's scope. For example instead of being long and flat, the body of the device could be cylindrical, with the grooves on the outside of the cylinder, or it could be disc-like with the grooves emanating from the center of the undersurface of the disc out toward the periphery. The grooves may be of different sizes or have walls that are of different angles with respect to the bottom surface of the device, etc.

Thus the scope of the invention should be limited by the appended claims and their legal equivalents, rather than by the examples given.

What is claimed is:

1. A vascular immobilizing device comprising in combination:
   (a) a flexible, elongated member having an elongated surface; and
   (b) a plurality of straight, generally transverse vein-stabilizing grooves in the elongated surface;
   (c) a first vein-stabilizing groove having a first depth and a first width, the first vein-stabilizing groove opening to subtend a first vein having a first diameter and located a first distance beneath a patient's skin when the elongated member is flexed in a first direction from an initial configuration and partially capturing the first vein and skin above it when the elongated member returns to the initial configuration to thereby stabilize the first vein, a second vein-stabilizing groove having a second depth and a second width, the second vein-stabilizing groove opening to subtend a second vein having a second diameter and located a second distance beneath a patient's skin when the elongated member is flexed in a second direction from an initial configuration and partially capturing the second vein and skin above it when the elongated member returns to the initial configuration to thereby stabilize the second vein.

2. The vascular immobilizer of claim 1 including at least the first and second vein-stabilizing grooves and a third vein-stabilizing groove, the first vein-stabilizing groove having opposed walls that are generally perpendicular to the elongated surface when the vascular immobilizer is in its initial configuration for immobilizing superficial veins, the second vein-stabilizing groove having opposed walls that are generally inclined approximately 60 degrees in opposed directions relative to the elongated surface for immobilizing intermediate depth veins, the third vein-stabilizing groove having opposed walls that are generally inclined approximately 45 degrees in opposed directions relative to the elongated surface for immobilizing deep veins.

3. The vascular immobilizer of claim 2 including a first group including the first, second, and third vein-stabilizing grooves, and including a second group including fourth, fifth, and sixth vein-stabilizing grooves that are similar to and proportionately smaller than the first, second, and third vein-stabilizing grooves, respectively.

4. The vascular immobilizer of claim 3 including a third group including seventh, eight, and ninth vein-stabilizing grooves that are similar to and proportionately smaller than the fourth, fifth, and sixth vein-stabilizing grooves, respectively.

5. The vascular immobilizer of claim 4 wherein the elongated member has similar trapezoidal cross-sections, which taper from a largest size at a first end of the elongated member to a smallest size at a second end of the elongated member, the elongated surface containing bases of the trapezoidal cross-sections.

6. The vascular immobilizer of claim 5 wherein the elongated member is composed of plastic material of sufficient elasticity and memory that the elongated member returns to the initial configuration when flexed in the first directions and then released.

7. The vascular immobilizer of claim 1 wherein at least one of the first and second vein-stabilizing grooves has roughened surfaces on opposed walls of that vein-stabilizing groove to improve gripping and capture of a vein and skin above it as the elongated member returns to its initial configuration.

8. The vascular immobilizer of claim 1 wherein the elongated member is composed of plastic material having sufficient memory to return to the initial configuration when released from a deformed configuration.

9. The vascular immobilizer of claim 1 wherein the elongated member is composed of transparent plastic material having sufficient memory to return to the initial configuration when released from a deformed configuration.

10. A method of stabilizing a vein for needle injection, comprising the steps of:
   (a) providing a vascular stabilizing device including a flexible, elongated member having an elongated surface and a plurality of straight, generally transverse vein-stabilizing grooves in the elongated surface;
   (b) selecting a first groove in accordance with the diameter and depth of a vein to be stabilized;
   (c) flexing the elongated member from an initial configuration to open the first groove wider;
   (d) positioning the elongated member so the opened first groove subtends the vein and opposed edges of the first groove engage skin above and on either side of the vein;
   (e) unflexing the elongated member to partially close the first groove using it to grip and partially capture the vein and the skin above it to thereby stabilize the vein;

11. The method of claim 10 wherein the vascular stabilizing device is transparent, the method including using one hand to hold the vascular stabilizing device in place to maintain the vein in a stabilized configuration and visualizing the stabilized vein through the vascular stabilizing device while inserting a needle into the stabilized vein.

12. The method of claim 10 wherein step (e) includes gripping the skin above the vein by means of roughened opposed walls of the first groove to force the skin above the vein and the vein into the first groove as it closes.

13. A vascular immobilizing device comprising in combination:
   (a) a flexible, elongated member having an elongated surface; and
   (b) a straight, generally transverse vein-stabilizing groove in the elongated surface; and
   (c) a vein stabilizing groove having a depth and a width, the vein stabilizing groove opening to subtend a vein having a diameter and located a distance beneath a patient's skin when the elongated member is flexed from an initial configuration and partially capturing the vein and skin above it when the elongated member returns to the initial configuration to thereby stabilize the first vein.

14. A method of stabilizing a vein for needle injection, comprising the steps of:
   (a) providing a vascular stabilizing device including a flexible, elongated member having an elongated surface and a straight, generally transverse vein-stabilizing groove in the elongated surface;
   (b) flexing the elongated member from an initial configuration to open the groove wider;
   (c) positioning the elongated member so the opened groove subtends the vein and opposed edges of the groove engage skin above and on either side of the vein; and
   (d) unflexing the elongated member to partially close the groove using it to grip and partially capture the vein and the skin above it to thereby stabilize the vein.

* * * * *